(12) United States Patent
Mullins et al.

(10) Patent No.: US 8,729,181 B2
(45) Date of Patent: May 20, 2014

(54) AROMATIC POLYCYANATE COMPOUNDS AND PROCESS FOR THE PRODUCTION THEREOF

(75) Inventors: Michael J. Mullins, Houston, TX (US); Robert E. Hefner, Jr., Rosharon, TX (US); Ulrich Herold, Buehl (DE); Mark B. Wilson, Clute, TX (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 12/921,699

(22) PCT Filed: Mar. 9, 2009

(86) PCT No.: PCT/US2009/036527
§ 371 (c)(1),
(2), (4) Date: Sep. 9, 2010

(87) PCT Pub. No.: WO2009/114469
PCT Pub. Date: Sep. 17, 2009

(65) Prior Publication Data
US 2011/0009562 A1    Jan. 13, 2011

Related U.S. Application Data

(60) Provisional application No. 61/035,820, filed on Mar. 12, 2008.

(51) Int. Cl.
*C08L 61/06*    (2006.01)
*C07C 39/16*    (2006.01)
*C08G 8/04*     (2006.01)

(52) U.S. Cl.
USPC ............ 524/595; 568/720; 528/165; 525/504

(58) Field of Classification Search
None
See application file for complete search history.

(56) References Cited

U.S. PATENT DOCUMENTS

| | | | |
|---|---|---|---|
| 3,689,440 A | | 9/1972 | Glaesmann |
| 3,694,410 A | | 9/1972 | Oehmke et al. |
| 4,022,755 A | * | 5/1977 | Tanigaichi et al. ............ 525/504 |
| 4,094,852 A | * | 6/1978 | Sundermann et al. ........ 524/710 |
| 4,110,364 A | * | 8/1978 | Gaku et al. ..................... 528/170 |
| 4,709,008 A | * | 11/1987 | Shimp ........................... 528/422 |
| 5,138,101 A | | 8/1992 | Devon |
| 5,146,006 A | * | 9/1992 | Li ................................. 568/720 |
| 5,191,128 A | * | 3/1993 | Li ................................. 568/720 |
| 6,252,121 B1 | | 6/2001 | Argyropoulos et al. |
| 6,555,517 B1 | | 4/2003 | Markert et al. |

FOREIGN PATENT DOCUMENTS

| | | |
|---|---|---|
| EP | 0564259 A2 | 10/1993 |
| JP | 04 343359 A * | 11/1992 |
| JP | 04343359 A | 11/1992 |
| JP | 2002-212109 A | 7/2002 |

OTHER PUBLICATIONS

Perry, J. Org. Chem., 1959, pp. 829-833, vol. 42.
T. Fang and D.A. Shimp, Progess in Polymer Sci., pp. 61-118, vol. 20.
Martin & Bauer, Organic Synthesis, (1983), pp. 35-68 vol. 61, John Wiley and Sons.
U.S. Appl. No. 61/035,823.
U.S. Appl. No. 61/035,810.
U.S. Appl. No. 61/035,816.

* cited by examiner

*Primary Examiner* — Randy Gulakowski
*Assistant Examiner* — Jeffrey Washville

(57) ABSTRACT

Aromatic polycyanate compounds which comprise cycloaliphatic moieties, a process for the production thereof and resins and thermoset products which are based on these compounds.

27 Claims, No Drawings

AROMATIC POLYCYANATE COMPOUNDS AND PROCESS FOR THE PRODUCTION THEREOF

BACKGROUND OF THE INVENTION

1. Field of the Invention

The present invention relates generally to aromatic polycyanate compounds which comprise cycloaliphatic moieties and mixtures of such compounds, a process for the production thereof, and to resins and thermoset products which are based on these compounds.

2. Discussion of Background Information

The cyanate derivatives of polyfunctional phenols have been prized for their combination of high glass transition temperature (Tg), high use temperatures, and good dielectric properties. The polyfunctional phenols are typically prepared by condensation of formaldehyde with phenols. This is a versatile method for producing polyphenolic compounds (or novolacs) that have many applications, such as epoxy hardeners and starting materials to make high performance epoxy resins. One undesirable feature of this chemistry is that there are many products formed from this condensation with a broad distribution of molecular weights. The product distribution is a function of the starting molar ratio of formaldehyde to phenol, catalyst, and other process parameters.

In order to produce a product with high functionality (at least 4 phenols per molecule on average) a material with a high polydispersity (Mw/Mn) inevitably results. Typical polydispersities of 3 to 6 are obtained. As a consequence, high functionality products typically have high molecular weights, and therefore the viscosities are high. High viscosity is a disadvantage in many applications such as casting, coating, and adhesive bonding.

Another example of a high functionality novolac is bisphenol A novolac (BPAN) made from bisphenol A and formaldehyde. Again, in order to obtain high functionality, high polydispersities (typically 2.5-5.5) and high viscosities must be tolerated. In the case of BPAN, it is difficult to remove unreacted bisphenol A, and therefore commercially available BPAN's are typically contaminated with ~20 wt % bisphenol A. Conversion of these high functionality novolacs to cyanate esters therefore gives a high viscosity material. The reaction of bisphenol A and formaldehyde and the conversion of the resultant mixture of polyphenolic compounds into a mixture of polycyanate compounds can schematically be represented as follows:

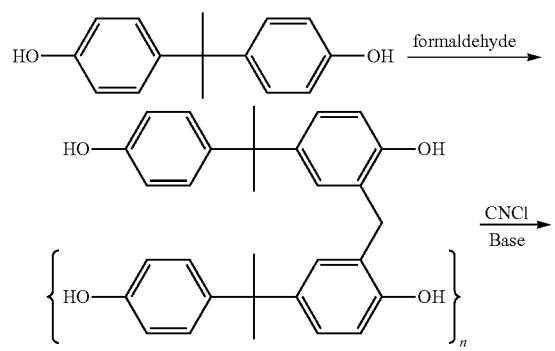

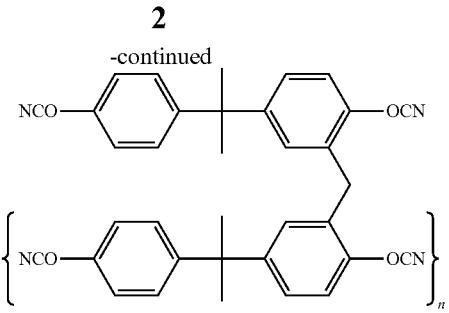

SUMMARY OF THE INVENTION

The present inventors have now unexpectedly found a method by which high functionality cyanate esters (hereafter also referred to as "mixture of polycyanate compounds") with low polydispersity (and thus relatively low viscosity) can be prepared. This method can schematically be represented with idealized structures as follows (for the case where cyclohexane dialdehyde and phenol are used as starting materials):

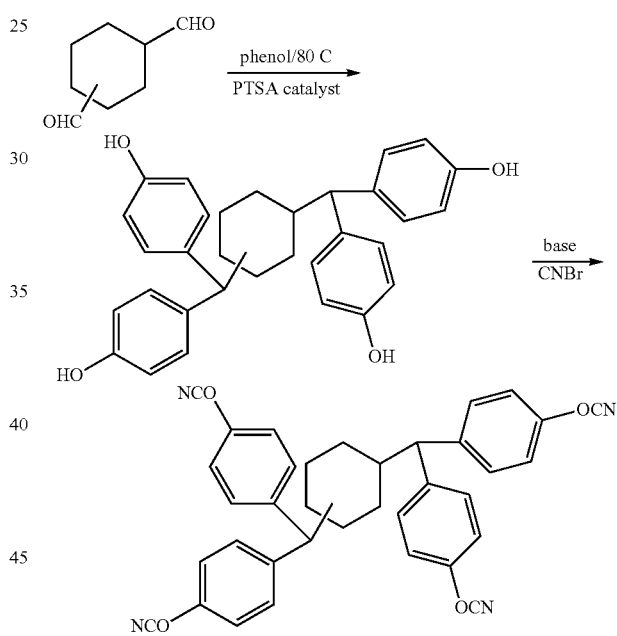

The present invention provides a process for preparing a mixture of polyphenolic compounds having a polydispersity of not higher than about 2. The process comprises the condensation of a dialdehyde of a cycloalkane having from about 5 to about 24 ring carbon atoms with a phenolic compound at a ratio of phenolic hydroxy groups to aldehyde groups which affords a mixture of polyphenolic compounds with a polydispersity of not higher than about 2.

In one aspect of the process, the ratio of the number of phenolic hydroxy groups to the number of aldehyde groups may be at least about 4.

In another aspect of the process of the present invention, the cycloalkane dialdehyde may have from 6 to about 19 ring carbon atoms, e.g., 6, 7, or 8 ring carbon atoms. For example, the cycloalkane dialdehyde may comprise one or more cyclohexane dialdehyde isomers.

In another aspect of the process, the phenolic compound may comprise (unsubstituted) phenol.

The present invention also provides a mixture of polyphenolic compounds which is obtainable by the process of the present invention as set forth above (including the various aspects thereof).

In one aspect, the mixture of polyphenolic compounds may have a polydispersity of not higher than about 1.5.

In another aspect, the average number of hydroxy groups per molecule in the mixture may be at least about 6.

The present invention also provides a process for preparing a mixture of polycyanate compounds which has a polydispersity of not higher than about 2. The process comprises partially or completely converting the phenolic hydroxy groups which are present in the mixture of polyphenolic compounds of the present invention as set forth above (including the various aspects thereof) into cyanate (—OCN) groups.

In one aspect, the process may comprise contacting the mixture of polyphenolic compounds with a cyanogen halide.

In another aspect of the process, substantially all of the phenolic hydroxy groups which are present in the starting mixture may be converted into cyanate groups.

The present invention also provides a mixture of polycyanate compounds which is obtainable by the process of the present invention as set forth above (including the various aspects thereof).

The present invention also provides a first polymerizable mixture which comprises (i) the mixture of polycyanate compounds of the present invention as set forth above and/or a prepolymerized form thereof and (ii) at least one compound and/or prepolymer thereof which is capable of reacting with (i).

In one aspect of the first polymerizable mixture, the at least one compound (ii) may be selected from one or more of aromatic di- and polycyanates which are different from the polycyanates present in (i), aromatic di- and polycyanamides, di- and polymaleimides, and di- and polyglycidyl ethers.

In another aspect, the first polymerizable mixture may further comprise one or more substances which are selected from polymerization catalysts, co-curing agents, flame retardants, synergists for flame retardants, solvents, fillers, glass fibers, adhesion promoters, wetting aids, dispersing aids, surface modifiers, thermoplastic polymers, and mold release agents.

In yet another aspect, the first polymerizable mixture may be partially or completely cured.

The present invention also provides a second polymerizable mixture which comprises (i) the mixture of polycyanate compounds of the present invention as set forth above and/or a prepolymerized form thereof and (ii) one or more substances which are selected from polymerization catalysts, co-curing agents, flame retardants, synergists for flame retardants, solvents, fillers, glass fibers, adhesion promoters, wetting aids, dispersing aids, surface modifiers, thermoplastic polymers, and mold release agents.

In one aspect, the second polymerizable mixture may be partially or completely cured.

The present invention also provides a product which comprises the first or second polymerizable mixtures as set forth above (including the various aspects thereof), preferably in at least partially or substantially completely cured form.

In one aspect, the product may be at least one of an electrical laminate, an IC (integrated circuit) substrate, a casting, a coating, a die attach and mold compound formulation, a composite, and an adhesive.

The present invention also provides a tetraphenolic compound of formula (I):

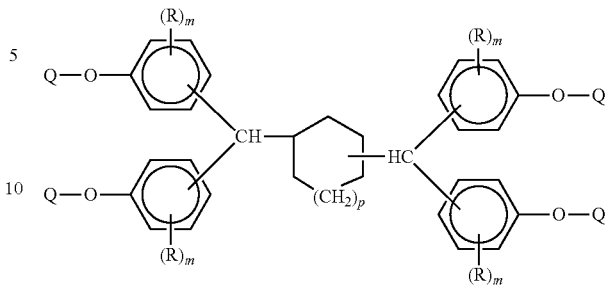

wherein:
p is 0 or an integer of from 1 to about 19;
each m independently is 0, 1, or 2;
the moieties R independently represent halogen, cyano, nitro, unsubstituted or substituted alkyl preferably having from 1 to about 6 carbon atoms, unsubstituted or substituted cycloalkyl preferably having from about 5 to about 8 carbon atoms, unsubstituted or substituted alkoxy preferably having from 1 to about 6 carbon atoms, unsubstituted or substituted alkenyl preferably having from 3 to about 6 carbon atoms, unsubstituted or substituted alkenyloxy preferably having from 3 to about 6 carbon atoms, unsubstituted or substituted aryl preferably having from 6 to about 10 carbon atoms, unsubstituted or substituted aralkyl preferably having from 7 to about 12 carbon atoms, unsubstituted or substituted aryloxy preferably having from 6 to about 10 carbon atoms, and unsubstituted or substituted aralkyloxy preferably having from 7 to about 12 carbon atoms; and
the moieties Q independently represent hydrogen, —CN, alkyl, alkenyl, aryl, aralkyl, and acyl;
and any non-aromatic cyclic moieties comprised in the above formula (I) may optionally carry one or more substituents and/or may optionally comprise one or more double bonds.

In one aspect of the tetraphenolic compound, the moieties Q may be identical and/or all moieties Q may represent hydrogen or substantially all moieties Q may represent —CN (giving rise to cyanate groups —OCN).

In another aspect, p in the above formula (I) may have a value of from 1 to about 14. For example, p may have a value of 1, 2, or 3 and may in particular, equal 1.

In yet another aspect, each m in formula (I) may independently be 0 or 1.

In a still further aspect, the compound of formula (I) may be dimethylcyclohexane tetraphenol, or dimethylcyclohexane tetraphenol tetracyanate.

The present invention also provides a mixture of polyphenolic and/or polycyanate compounds which comprises the compound of formula (I) of the present invention set forth above (including the various aspects thereof), preferably in combination with structurally related compounds of a higher degree of condensation.

Other features and advantages of the present invention will be set forth in the description of invention that follows, and will be apparent, in part, from the description or may be learned by practice of the invention. The invention will be realized and attained by the compositions, products, and methods particularly pointed out in the written description and claims hereof.

DETAILED DESCRIPTION OF THE PRESENT INVENTION

Unless otherwise stated, a reference to a compound or component includes the compound or component by itself, as well as in combination with other compounds or components, such as mixtures of compounds.

As used herein, the singular forms "a," "an," and "the" include the plural reference unless the context clearly dictates otherwise.

Except where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not to be considered as an attempt to limit the application of the doctrine of equivalents to the scope of the claims, each numerical parameter should be construed in light of the number of significant digits and ordinary rounding conventions.

Additionally, the recitation of numerical ranges within this specification is considered to be a disclosure of all numerical values and ranges within that range. For example, if a range is from about 1 to about 50, it is deemed to include, for example, 1, 7, 34, 46.1, 23.7, or any other value or range within the range.

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show embodiments of the present invention in more detail than is necessary for the fundamental understanding of the present invention, the description making apparent to those skilled in the art how the several forms of the present invention may be embodied in practice.

As set forth above, the present invention provides, inter alia, a process for preparing a mixture of polyphenolic compounds having a polydispersity (Mw/Mn; Mw=weight average molecular weight and Mn=number average molecular weight) of not higher than about 2, e.g., not higher than about 1.8, not higher than about 1.5, or not higher than about 1.3 and/or with an average number of hydroxy groups per molecule in the mixture of at least about 4, e.g., at least about 4.5, at least about 5, at least about 5.5, or at least about 6. The process comprises the condensation of a dialdehyde of a cycloalkane having from about 5 to about 24 ring carbon atoms with a phenolic compound at a ratio of phenolic hydroxy groups to aldehyde groups which affords a mixture of polyphenolic compounds with the desired polydispersity. The ratio of the number of phenolic hydroxy groups to the number of aldehyde groups employed in the reaction will often be at least about 4, e.g., at least about 5, at least about 5.5, or at least about 6, or even at least about 6.5.

The cycloalkane dicarboxaldehyde which is used as a starting material in the above process may have from 5 to about 19 ring carbon atoms, e.g., up to about 12 or up to about 10 ring carbon atoms, e.g., 6, 7, 8, or 9 ring carbon atoms. For example, the cycloalkane dicarboxaldehyde may comprise one or more isomers (including regioisomers and stereoisomers) of a specific dicarboxaldehyde. By way of non-limiting example, in the case of cyclohexane dicarboxaldehyde isomers, one or more of cis-cyclohexane-1,3-dicarboxaldehyde, trans-cyclohexane-1,3-dicarboxaldehyde, cis-cyclohexane-1,4-dicarboxaldehyde and trans-cyclohexane-1,4-dicarboxaldehyde may be employed (although it is also possible to employ cis and/or trans-cyclohexane-1,2-dicarboxaldehyde). Also, a mixture of two or more dicarboxaldehydes which differ, e.g., in the number of ring carbon atoms and/or in the presence or absence, number and/or types of ring substituents (for example, a mixture of one or more cyclohexane dicarboxaldehyde isomers and one or more cyclooctane dicarboxaldehyde isomers) may be employed in the process of the present invention.

The cycloalkane moiety of the dicarboxaldehyde for use in the process of the present invention may comprise one or more (e.g., 1, 2, 3, or 4) double bonds and/or may optionally carry one or more (e.g., 1, 2, or 3) additional substituents. If more than one substituent is present, the substituents may be the same or different. Non-limiting examples of substituents which may be present on the cycloalkane ring are alkyl groups, e.g., optionally substituted alkyl groups having from 1 to about 6 carbon atoms (e.g. methyl or ethyl), optionally substituted aryl (in particular, optionally substituted phenyl), and halogen atoms such as, e.g., F, Cl, and Br. The alkyl and aryl groups may be substituted with, e.g., one or more halogen atoms such as, e.g., F, Cl, and Br.

The phenolic compound for use in the above process may be (unsubstituted) phenol. Moreover, the aromatic ring of phenol may comprise one or more (e.g., 1, 2, 3 or 4) substituents, for example one or two substituents. If two or more substituents are present, they may be the same or different. Non-limiting examples of substituents which may be present on the phenol ring are halogen (e.g., F, Cl, and Br, preferably Cl or Br), cyano, nitro, unsubstituted or substituted alkyl preferably having from 1 to about 6 carbon atoms, unsubstituted or substituted cycloalkyl preferably having from about 5 to about 8 carbon atoms, unsubstituted or substituted alkoxy preferably having from 1 to about 6 carbon atoms, unsubstituted or substituted alkenyl preferably having from 3 to about 6 carbon atoms, unsubstituted or substituted alkenyloxy preferably having from 3 to about 6 carbon atoms, unsubstituted or substituted aryl preferably having from 6 to about 10 carbon atoms, unsubstituted or substituted aralkyl preferably having from 7 to about 12 carbon atoms, unsubstituted or substituted aryloxy preferably having from 6 to about 10 carbon atoms, and unsubstituted or substituted aralkoxy preferably having from 7 to about 12 carbon atoms.

It is to be appreciated that whenever the terms "alkyl" and "alkenyl" are used in the present specification and the appended claims, these terms also include the corresponding cylcoaliphatic groups such as, e.g., cyclopentyl, cyclohexyl, cyclopentenyl, and cyclohexenyl. Also, where two alkyl and/or alkenyl groups are attached to two carbon atoms of an aliphatic or aromatic ring, they may be combined to form an alkylene or alkenylene group which together with the carbon atoms to which this group is attached results in a preferably 5- or 6-membered ring structure. In the case of non-adjacent carbon atoms, this ring structure may give rise to a bicyclic compound.

The above alkyl groups and alkoxy groups will often comprise from 1 to about 4 carbon atoms and in particular, 1 or 2 carbon atoms. Non-limiting specific examples of these groups include methyl, ethyl, propyl, isopropyl, n-butyl, isobutyl, sec-butyl, and tert-butyl, and methoxy, ethoxy, propoxy, isopropoxy, n-butoxy, isobutoxy, sec-butoxy, and tert-butoxy. The alkyl and alkoxy groups may be substituted with one or more (e.g. 1, 2 on 3) substituents. If more than one substituent is present, the substituents may be the same or different and are preferably identical. Non-limiting examples of these substituents include halogen atoms such as, e.g., F, Cl, and Br. Non-limiting examples of substituted alkyl and alkoxy groups include $CF_3$, $CF_3CH_2$, $CCl_3$, $CCl_3CH_2$, $CHCl_2$, $CH_2Cl$, $CH_2Br$, $CCl_3O$, $CHCl_2O$, $CH_2ClO$, and $CH_2BrO$.

The above alkenyl and alkenyloxy groups will often comprise 3 or 4 carbon atoms and in particular, 3 carbon atoms. Non-limiting specific examples of these groups are allyl, methallyl and 1-propenyl. The alkenyl and alkenyloxy groups may be substituted with one or more (e.g., 1, 2, or 3) substituents. If more than one substituent is present, the substituents may be the same or different and are preferably identical. Non-limiting examples of these substituents include halogen atoms such as, e.g., F, Cl, and Br.

The above aryl and aryloxy groups will often be phenyl and phenoxy groups. The aryl and aryloxy groups may be substituted with one or more (e.g., 1, 2, 3, 4, or 5) substituents. If more than one substituent is present, the substituents may be the same or different. Non-limiting examples of these substituents include nitro, cyano, halogen such as, e.g., F, Cl, and Br, optionally halogen-substituted alkyl having from 1 to about 6 carbon atoms, e.g., from 1 to about 4 carbon atoms (for example, methyl or ethyl) and optionally halogen-substituted alkoxy having from 1 to about 6 carbon atoms, e.g., from 1 to about 4 carbon atoms (for example, methoxy or ethoxy). Non-limiting specific examples of substituted aryl and aryloxy groups include, tolyl, xylyl, ethylphenyl, chlorophenyl, bromophenyl, tolyloxy, xylyloxy, ethylphenoxy, chlorophenoxy, and bromophenoxy.

The above aralkyl and aralkoxy groups will often be benzyl, phenethyl, benzyloxy, or phenethoxy groups. These groups may be substituted (preferably on the aryl ring, if at all) with one or more (e.g., 1, 2, 3, 4 or 5) substituents. If more than one substituent is present, the substituents may be the same or different. Non-limiting examples of these substituents include nitro, cyano, halogen such as, e.g., F, Cl, and Br, optionally halogen-substituted alkyl having from 1 to about 6 carbon atoms, e.g., from 1 to about 4 carbon atoms (for example, methyl or ethyl), and optionally halogen-substituted alkoxy having from 1 to about 6 carbon atoms, e.g., from 1 to about 4 carbon atoms (for example, methoxy or ethoxy).

Of course, as in the case of the dicarboxaldehyde, two or more different phenolic compounds may be employed in the process of the present invention (e.g., phenol and a substituted phenol or two differently substituted phenol compounds), although this is usually not preferred.

The cycloaliphatic dicarboxaldehydes which are starting materials for the process for preparing the mixture of polyphenolic compounds of the present invention may be prepared by methods which are well known to those of skill in the art. By way of non-limiting example, cyclohexane (1,3 and/or 1,4-)dicarboxaldehyde can be produced, e.g., by hydroformylation of a cyclohexene carboxaldehyde, which in turn can be prepared by a Diels-Alder reaction of a conjugated diene such as, e.g., butadiene, piperylene, isoprene and chloroprene with an optionally substituted alpha,beta-unsaturated aldehyde such as, e.g., acrolein, methacrolein, crotonaldehyde or cinnamaldehyde as the dienophile. In this regard, U.S. Pat. No. 6,252,121 and Japanese patent application JP 2002-212109, the entire disclosures whereof are incorporated by reference herein, may, for example, be referred to. These (in no way limiting) reactions may be schematically represented as follows:

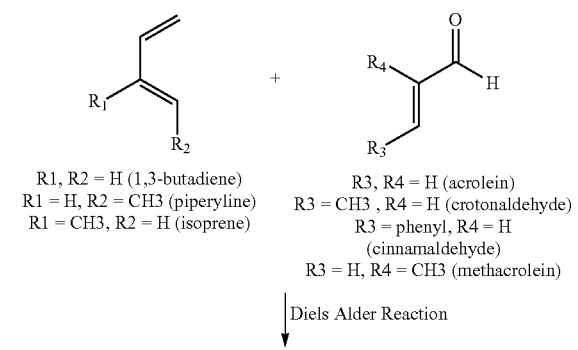

R1, R2 = H (1,3-butadiene)
R1 = H, R2 = CH3 (piperyline)
R1 = CH3, R2 = H (isoprene)

R3, R4 = H (acrolein)
R3 = CH3, R4 = H (crotonaldehyde)
R3 = phenyl, R4 = H (cinnamaldehyde)
R3 = H, R4 = CH3 (methacrolein)

Diels Alder Reaction

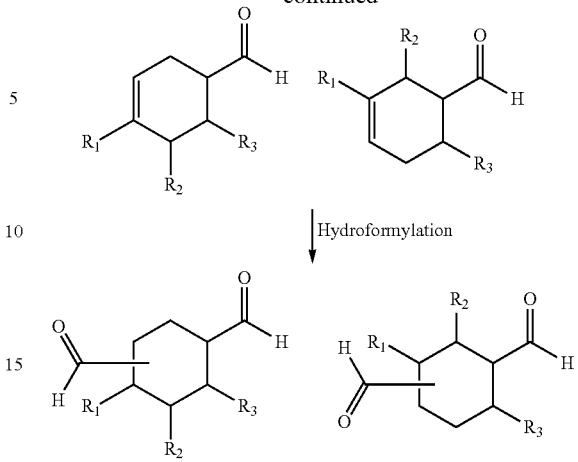

Hydroformylation

By using cyclic dienes such as, e.g., cyclopentadiene, cyclohexadiene or furan as conjugated diene in the Diels-Alder reaction, bicyclic unsaturated aldehydes may be obtained, as illustrated in the following scheme:

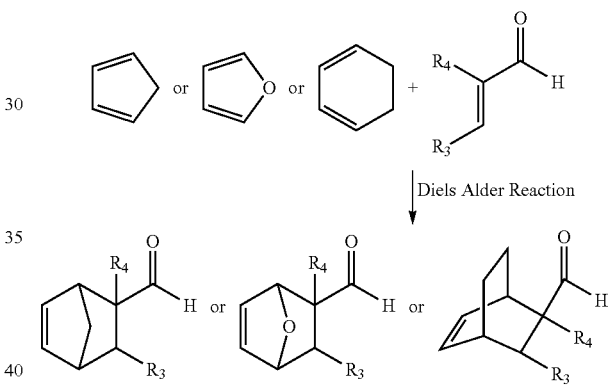

Diels Alder Reaction

Cycloaliphatic dicarboxaldehydes may also be prepared by hydroformylation of cyclic diolefins such as, e.g., cyclooctadiene, as described in, for example U.S. Pat. No. 5,138,101 and DE 198 14 913, or by ozonolysis of bicyclic olefins such as norbornene to produce cyclopentane dicarboxaldehyde (see, e.g., Perry, J. Org. Chem., 42, 829-833, 1959). The entire disclosures of these three documents are incorporated by reference herein.

The condensation of a cycloalkane dicarboxaldehyde (or a mixture of cycloalkane dicarboxaldehydes) with, e.g., (unsubstituted) phenol affords a mixture of polyphenolic compounds which comprises a cycloalkane dicarboxaldehyde tetraphenol along with compounds with a higher (and lower) degree of condensation. In general, the process of the present invention will afford a product which comprises or essentially consists of a compound of formula (I) (wherein Q=H) set forth above.

In the above formula (I), p is 0 or an integer of from 1 to about 19, e.g., up to about 14, up to about 12 or up to about 8 such as, e.g., 1, 2, 3, 4, 5, 6, and 7, with 1, 2, or 3 being preferred and 1 being particularly preferred.

The cycloaliphatic moiety shown in formula (I) may comprise one or more (e.g., 1, 2, 3, or 4) double bonds and/or may carry one or more (e.g., 1, 2 or 3) substituents (although the cycloaliphatic moiety will usually not comprise any double bonds or substituents). If more than one substituent is present, the substituents may be the same or different. Non-limiting examples of substituents which may be present on the cycloaliphatic moiety are alkyl groups, e.g., optionally substituted alkyl groups having from 1 to about 6 carbon atoms (e.g., methyl or ethyl), and halogen such as, e.g., F, Cl, and Br. The alkyl groups may be substituted with, e.g., one or more halogen atoms such as, e.g., F, Cl, and Br.

The value of each m in the above formula (I) independently is 0, 1, or 2. Preferably, the values of m are identical. Also preferably, m equals 0 or 1.

The moieties R in the above formula (I) independently represent halogen (e.g., F, Cl, and Br, preferably Cl or Br), cyano (—CN), nitro, unsubstituted or substituted alkyl preferably having from 1 to about 6 carbon atoms, unsubstituted or substituted cycloalkyl preferably having from about 5 to about 8 carbon atoms, unsubstituted or substituted alkoxy preferably having from 1 to about 6 carbon atoms, unsubstituted or substituted alkenyl preferably having from 3 to about 6 carbon atoms, unsubstituted or substituted alkenyloxy preferably having from 3 to about 6 carbon atoms, unsubstituted or substituted aryl preferably having from 6 to about 10 carbon atoms, unsubstituted or substituted aralkyl preferably having from 7 to about 12 carbon atoms, unsubstituted or substituted aryloxy preferably having from 6 to about 10 carbon atoms, and unsubstituted or substituted aralkoxy preferably having from 7 to about 12 carbon atoms.

Regarding exemplary and preferred meanings of the moieties R the comments set forth above with respect to the substituents on the substituted phenol starting material of the process of the present invention apply in their entirety and may be referred to.

The moieties Q in the above formula (I) independently represent hydrogen, —CN, alkyl, alkenyl, aryl, aralkyl, and acyl. Non-limiting examples of alkyl groups are groups having from 1 to about 6 carbon, preferably from 1 to about 4 carbon atoms such as, e.g., methyl, ethyl, and propyl. These groups may optionally be substituted by one or more (e.g., 1, 2, or 3) substituents such as, for example halogen (e.g., F, Cl, and Br).

Non-limiting examples of alkenyl groups Q include those of formula $HR^1C=CR^1—CH_2—$ or $H_2R^1C—CR^1=HC—$ wherein the moieties $R^1$ independently represent hydrogen or unsubstituted or substituted (preferably unsubstituted) alkyl having from 1 to about 3 carbon atoms (e.g., methyl). Preferred alkenyl moieties Q include allyl (2-propenyl), methallyl (2-methyl-2-propenyl), and 1-propenyl.

Non-limiting examples of aryl groups Q include phenyl and phenyl which is substituted by 1, 2, 3, 4, or 5 substituents. Preferred examples of substituents (which may be the same or different) include halogen, nitro, cyano, halogen such as F, Cl, and Br, optionally halogen-substituted alkyl having from 1 to about 6 carbon atoms, and optionally halogen-substituted alkoxy having from 1 to about 6 carbon atoms.

Non-limiting aralkyl groups include benzyl and phenethyl wherein the phenyl rings may optionally be substituted by 1, 2, 3, 4, or 5 substituents. Preferred examples of substituents (which may be the same or different) include halogen, nitro, cyano, halogen such as F, Cl, and Br, optionally halogen-substituted alkyl having from 1 to about 6 carbon atoms, and optionally halogen substituted alkoxy having from 1 to about 6 carbon atoms.

Non-limiting examples of acyl groups include alkanoyl having from 1 to about 6 carbon atoms such as, e.g., formyl, acetyl, propionyl, and butyryl, and groups of formulae $HR^1C=CR^1—CH_2—C(=O)—$ and $H_2R^1C—CR^1=HC—C(=O)—$ wherein the moieties $R^1$ independently represent hydrogen or unsubstituted or substituted (preferably unsubstituted) alkyl having from 1 to about 3 carbon atoms (for example, methyl) such as, e.g., acryloyl, and methacryloyl.

The present process renders it possible to produce very low polydispersity products with a high average functionality. For example, when cyclohexane dicarboxaldehyde and phenol are employed as starting materials in the process of the present invention, products having a weight average molecular weight (Mw) of about 930 and a number average molecular weight (Mn) of about 730 and/or an average of about 6 hydroxy groups per molecule can routinely be produced. The process uses a relatively high molar ratio of aromatic hydroxy group to aldehyde functionality to keep oligomerization low. The excess phenolic starting material may then be removed, for example, by distillation.

The conversion of the phenolic hydroxy groups in the mixture of polyphenolic compounds into cyanate or other groups is possible using conventional processes. Regarding the conversion of phenolic hydroxyl groups into cyanate groups see, for example, T. Fang and D. A. Shimp in Progress in Polymer Sci., vol. 20, pp. 61-118. Regarding the conversion of phenolic hydroxyl groups into alkenyl ether groups (e.g. allyl ether groups) see, e.g., the co-assigned application entitled "ETHYLENICALLY UNSATURATED MONOMERS COMPRISING ALIPHATIC AND AROMATIC MOIETIES", filed concurrently herewith. Regarding the conversion of phenolic hydroxyl groups into glycidyl ether groups see, e.g., the co-assigned application entitled "POLYPHENOLIC COMPOUNDS AND EPOXY RESINS COMPRISING CYLCOALIPHATIC MOIETIES AND PROCESS FOR THE PRODUCTION THEREOF", filed concurrently herewith. The entire disclosures of the above documents are expressly incorporated by reference herein.

By way of non-limiting example, for preparing a mixture of polycyanates the mixture of polyphenolic compounds prepared by the process of the present invention may be reacted with an about stoichiometric quantity or a slight stoichiometric excess (up to about 20 percent excess) of a cyanogen halide per phenolic hydroxy group, in the presence of an about stoichiometric quantity or a slight stoichiometric excess (up to about 20 percent excess) of a base compound per phenolic hydroxy group, and in the presence of a suitable solvent.

Usually reaction temperatures of from about −40° C. to about 60° C. are employed, with reaction temperatures of from about −15° C. to about 10° C. being preferred and reaction temperatures of from about −10° C. to about 0° C. being particularly preferred. Reaction times can vary substantially, for example, as a function of the reactants being employed, reaction temperature, solvent(s) used, the scale of the reaction, and the like, but are often in the range of from about 15 minutes to about 4 hours, with reaction times of from about 30 minutes to about 90 minutes being preferred.

Non-limiting examples of suitable cyanogen halides include cyanogen chloride and cyanogen bromide. Alternately, the method of Martin and Bauer described in Organic Synthesis, volume 61, pages 35-68 (1983), published by John Wiley and Sons, the entire disclosure of which is expressly incorporated by reference herein, can be used to generate the cyanogen halide in situ from sodium cyanide and a halogen such as chlorine or bromine.

Non-limiting examples of suitable base compounds for use in the cyanation process include both inorganic bases and tertiary amines such as sodium hydroxide, potassium hydroxide, trimethylamine, triethylamine, and mixtures thereof. Triethylamine is most preferred as the base.

Non-limiting examples of suitable solvents for the cyanation reaction include water, aliphatic ketones, chlorinated hydrocarbons, aliphatic and cycloaliphatic ethers and diethers, aromatic hydrocarbons, and mixtures thereof. Acetone, methylethylketone, methylene chloride, and chloroform are particularly suitable as the solvent.

The mixture of polycyanate compounds of the present invention can usually be cured (thermoset) by heating at a temperature of from about 50° C. to about 400° C., preferably by heating at a temperature of from about 100° C. to about 250° C., optionally in the presence of a suitable catalyst. Examples of suitable catalysts include acids, bases, salts, nitrogen compounds and phosphorus compounds, such as for example, Lewis acids such as, e.g., $AlCl_3$, $BF_3$, $FeCl_3$, $TiCl_4$, $ZnCl_2$, $SnCl_4$; protonic acids such as HCl, $H_3PO_4$; aromatic hydroxy compounds such as phenol, p-nitrophenol, pyrocatechol, dihydroxynaphthalene; sodium hydroxide, sodium methylate, sodium phenolate, trimethylamine, triethylamine, tributylamine, diazabicyclo[2.2.2]octane, quinoline, isoquinoline, tetrahydroisoquinoline, tetraethylammonium chloride, pyridine-N-oxide, tributyl phosphine, zinc octoate, tin octoate, zinc naphthenate, cobalt naphthenate, cobalt octoate, cobalt acetylacetonate, and the like. Also suitable as catalysts are metal chelates such as, for example, the chelates of transition metals and bidentate or tridentate ligands, particularly the chelates of iron, cobalt, zinc, copper, manganese, zirconium, titanium, vanadium, aluminum, and magnesium. These and other catalysts are disclosed in U.S. Pat. Nos. 3,694,410 and 4,094,852, the entire disclosures of which are incorporated by reference herein. Cobalt naphthenate, cobalt octoate, and cobalt acetylacetonate are particularly useful as the catalysts.

The quantity of catalyst(s) used, if any, may depend on the structure of the particular catalyst(s), the structure of the polycyanate compounds being cured, the cure temperature, the cure time, and the like. Generally, catalyst concentrations of from about 0.001 to about 2 percent by weight, based on the total weight of the polymerizable (curable) components present, are preferred.

B-staging or prepolymerization of the mixture of polycyanate compounds of the present invention can be accomplished by using lower temperatures and/or shorter curing times than those set forth above. Curing of a thus formed B-staged (prepolymerized) resin can then be accomplished at a later time or immediately following B-staging (prepolymerization) by increasing the temperature and/or the cure time.

The cured (thermoset) products prepared from the mixture of polycyanate compounds of the present invention comprise the cyanate group homopolymerization structure, i.e., the 1,3,5-triazine ring, unless other functionalities are present in the curable mixture that participate in the curing process and prevent the formation of the 1,3,5-triazine ring structure.

The aromatic dicyanate compounds of the present invention may be copolymerized with a variety of other compounds and/or prepolymers thereof. In corresponding copolymerizable mixtures the mixture of polycyanate compounds and/or a prepolymer form thereof may, for example, be present in quantities of from about 5% to about 95% by weight, e.g., from about 10% to about 90% by weight or from about 25% to about 75% by weight, based on the total weight of the polymerizable components.

Non-limiting examples of compounds (including prepolymers thereof) which may be copolymerized with the mixture of polycyanate compounds of the present invention (including tetracyanates of formula (I)) and/or prepolymer forms thereof include compounds which comprise one or more polymerizable ethylenically unsaturated moieties, aromatic di- and polycyanates which are different from the polycyanates of formula (I) and the compounds associated therewith, aromatic di- and polycyanamides, di- and polymaleimides, and di- and polyglycidyl ethers (epoxy resins) such as, e.g., diglycidyl ethers of bisphenol A or bisphenol F, glycidyl ethers of phenol novolac or cresol novolac resins, and the epoxy resins disclosed in the coassigned application entitled "POLYPHENOLIC COMPOUNDS AND EPOXY RESINS COMPRISING CYLCOALIPHATIC MOIETIES AND PROCESS FOR THE PRODUCTION THEREOF", filed concurrently herewith. Non-limiting specific examples of the use of dicyanates for making formulations which contain bismaleimides and epoxy resins and are useful for the production of high performance electrical laminates are disclosed in, e.g., U.S. Pat. No. 4,110,364, the entire disclosure of which is incorporated herein by reference.

It also is possible to copolymerize the mixture of polycyanate compounds of the present invention and/or a prepolymer form thereof with other components such as, e.g., one or more of (a) at least one compound which contains in the same molecule both a cyanate or cyanamide group and a polymerizable ethylenically unsaturated group; (b) at least one compound which contains in the same molecule both a 1,2-epoxide group and a polymerizable ethylenically unsaturated group; (c) at least one compound which contains in the same molecule both a maleimide group and a cyanate group; (d) at least one polyamine; and (e) at least one polyphenol, etc.

Specific and non-limiting examples of compounds (including prepolymers thereof) which may be copolymerized with the mixture of polycyanate compounds of the present invention include compounds of formula (II) and prepolymers thereof:

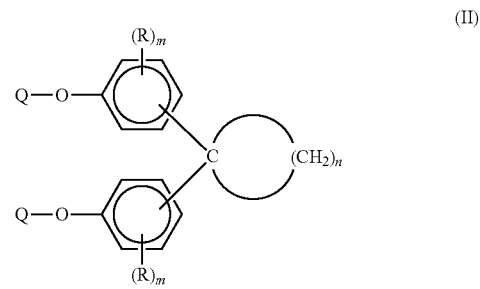

(II)

wherein:
n has a value of from about 5 to about 24;
each m independently is 0, 1, or 2;
the moieties R independently represent halogen, cyano, nitro, hydroxy, amino optionally carrying one or two alkyl groups preferably having from 1 to about 6 carbon atoms, unsubstituted or substituted alkyl preferably having from 1 to about 6 carbon atoms, unsubstituted or substituted cycloalkyl preferably having from about 5 to about 8 carbon atoms, unsubstituted or substituted alkoxy preferably having from 1 to about 6 carbon atoms, unsubstituted or substituted alkenyl preferably having from 3 to about 6 carbon atoms, unsubstituted or substituted alkenyloxy preferably having from 3 to about 6 carbon atoms, unsubstituted or substituted aryl preferably having from 6 to about 10 carbon atoms, unsubstituted or substituted aralkyl preferably having from 7 to about 12 carbon atoms, unsubstituted or substituted aryloxy preferably having from 6 to about 10 carbon atoms, and unsubstituted or substituted aralkoxy preferably having from 7 to about 12 carbon atoms; and the moieties Q independently represent hydrogen, cyano, $HR^1C=CR^1—CH_2—$, or $H_2R^1C—CR^1=HC—$ wherein the moieties $R^1$ independently represent hydrogen, or unsubstituted or substituted alkyl having from 1 to about 3 carbon atoms; with the proviso that when both moieties Q are hydrogen, at least one moiety R represents $HR^1C=CR^1—CH_2—$ or $H_2R^1C—CR^1=HC—$;

and any non-aromatic cyclic moieties comprised in the above formula (II) may optionally carry one or more substituents and/or may optionally comprise one or more double bonds and/or may optionally be polycyclic (e.g. bicyclic or tricyclic).

Regarding the cycloalkylidene moiety and the exemplary and preferred meanings of n, m, and R in formula (II) exactly the same applies as what has been set forth above with respect to the compounds of formula (I).

The moieties Q in the above formula (II) independently represent hydrogen, cyano, $HR^1C=CR^1—CH_2—$ or $H_2R^1C—CR^1=HC—$ wherein the moieties $R^1$ independently represent hydrogen, or unsubstituted or substituted (preferably unsubstituted) alkyl having from 1 to about 3 carbon atoms. A preferred moiety Q is allyl. Also, it is preferred for the moieties Q to be identical and to represent $HR^1C=CR^1—CH_2—$ or $H_2R^1C—CR^1=HC—$ and/or to be different from hydrogen. Also preferably, at least one of the moieties Q is not hydrogen.

Non-limiting specific examples of the above alkyl moieties $R^1$ include methyl, ethyl, propyl, and isopropyl. Methyl is preferred. If one or more substituents are present on these alkyl groups they may, for example, be halogen such as, e.g., F, Cl, and Br.

Non-limiting examples of the above compounds of formula (II) include 1,1-bis(4-hydroxyphenyl)cyclododecane bis(allyl ether), 1,1-bis(4-hydroxyphenyl)-cyclododecane bis(methallyl ether), 1,1-bis(4-hydroxyphenyl)-cyclododecane bis(1-propenyl ether), 1,1-bis(4-hydroxyphenyl)cyclodecane bis(allyl ether), 1,1-bis(4-hydroxyphenyl)cyclodecane bis(methallyl ether), 1,1-bis(4-hydroxyphenyl)-cyclodecane bis(1-propenyl ether), 2,2-bis(4-hydroxyphenyl)adamantane bis(allyl ether), 2,2-bis(4-hydroxyphenyl)adamantane bis(methallyl ether), 4,4'-bis(4-hydroxyphenyl)octahydro-1,4:5,8-dimethanonaphthalen-2(1H)ylidene bis(allyl ether), 4,4'-bis(4-hydroxyphenyl)octahydro-1,4:5,8-dimethanonaphthalen-2(1H)ylidene bis(methallyl ether), 5,5-bis(4-hydroxyphenyl)hexahydro-4,7-methanoindane bis(allyl ether) and 5,5-bis(4-hydroxyphenyl)hexahydro-4,7-methanoindane bis(methallyl ether), as well as 1,1-bis(4-cyanatophenyl) cyclododecane, 1,1-bis(4-cyanato-3,5-dimethylphenyl) cyclo-dodecane, 1,1-bis(4-cyanato-3-methylphenyl) cyclododecane, 1,1-bis(4-cyanatophenyl)cyclodecane, 2,2-bis(4-cyanatophenyl)adamantane, 4,4'-bis(4-cyanatophenyl) octahydro-1,4:5,8-dimethanonaphthalen-2(1H)ylidene and 5,5-bis(4-cyanatophenyl)hexahydro-4,7-methanoindane.

Further non-limiting examples of the above compounds of formula (II) include partial or complete Claisen rearrangement products of compounds of formula (II) wherein at least one of the moieties Q represents $HR^1C=CR^1—CH_2—$ or $H_2R^1C—CR^1=HC—$, as well as monomers which carry at least one substituent on at least one aromatic ring to block a Claisen rearrangement.

The compounds of formula (II) may prepared by methods which are well known to those of skill in the art. For example, these monomers may be prepared by etherification of a cycloalkane bisphenol of the above formula (II) wherein both moieties Q represent hydrogen with a compound which comprises a group $HR^1C=CR^1—CH_2—$ or $H_2R^1C—CR^1=HC—$ and/or by reaction with a cyanogen halide. For details in this regard see, e.g., the co-assigned application entitled "AROMATIC DICYANATE COMPOUNDS WITH HIGH ALIPHATIC CARBON CONTENT", filed concurrently herewith, the entire disclosure of which is expressly incorporated by reference herein, and the above-mentioned co-assigned application entitled "ETHYLENICALLY UNSATURATED MONOMERS COMPRISING ALIPHATIC AND AROMATIC MOIETIES".

Further specific and non-limiting examples of compounds (including prepolymers thereof) which may be copolymerized with the mixture of polycyanate compounds of the present invention include mixtures of compounds which correspond to the mixture of polycyanate compounds of the present invention wherein the cyanate groups are partially or completely replaced by groups of formulae $HR^1C=CR^1—CH_2—O—$ and/or $H_2R^1C—CR^1=HC—O—$ wherein the moieties $R^1$ independently represent hydrogen, or unsubstituted or substituted alkyl having from 1 to about 3 carbon atoms. Examples of corresponding groups include allyloxy, methallyloxy, and 1-propenyloxy.

Non-limiting specific examples of corresponding compounds which may be present in these mixtures include dimethylcyclohexane tetraphenol tetra(allyl ether), dimethylcyclohexane tetraphenol tetra(methallyl ether), dimethylcyclohexane tetraphenol tetra(1-propenyl ether), dimethylcyclooctane tetraphenol tetra(allyl ether), dimethylcyclooctane tetraphenol tetra(methallyl ether), dimethylcyclooctane tetraphenol tetra(1-propenyl ether), partial or complete Claisen rearrangement products of dimethylcyclohexane tetraphenol tetra(allyl ether), and compounds which carry at least one substituent on at least one aromatic ring to block a Claisen rearrangement.

The (co)polymerizable mixtures of the present invention and the products made therefrom respectively, may further comprise one or more other substances such as, e.g., one or more additives which are commonly present in polymerizable mixtures and products made therefrom. Non-limiting examples of such additives include polymerization catalysts, co-curing agents, flame retardants, synergists for flame retardants, solvents, fillers, adhesion promoters, wetting aids, dispersing aids, surface modifiers, thermoplastic resins, and mold release agents.

Non-limiting examples of co-curing agents for use in the present invention include dicyandiamide, substituted guanidines, phenolics, amino compounds, benzoxazine, anhydrides, amido amines, and polyamides.

Non-limiting examples of catalysts for use in the present invention (in addition to those set forth above with respect to the homopolymerization of the mixture of polycyanates include transition metal complexes, imidazoles, phosphonium salts, phosphonium complexes, tertiary amines, hydrazides, "latent catalysts" such as Ancamine 2441 and K61B (modified aliphatic amines available from Air Products), Ajinomoto PN-23 or MY-24, and modified ureas.

Non-limiting examples of flame retardants and synergists for use in the present invention include phosphorus containing molecules (DOP—epoxy reaction product), adducts of DOPO (6H-dibenz[c,e][1,2]oxaphosphorin-6-oxide), magnesium hydrate, zinc borate, and metallocenes.

Non-limiting examples of solvents for use in the present invention (for example, for improving processability) include acetone, methylethyl ketone, and Dowanol® PMA (propylene glycol methyl ether acetate available from Dow Chemical Company).

Non-limiting examples of fillers for use in the present invention include functional and non-functional particulate fillers with a particle size range of from about 0.5 nm to about 100 μm. Specific examples thereof include silica, alumina trihydrate, aluminum oxide, metal oxides, carbon nanotubes, silver flake or powder, carbon black, and graphite.

Non-limiting examples of adhesion promoters for use in the present invention include modified organosilanes (epoxidized, methacryl, amino, allyl, etc.), acetylacetonates, sulfur containing molecules, titanates, and zirconates.

Non-limiting examples of wetting and dispersing aids for use in the present invention include modified organosilanes such as, e.g., Byk 900 series and W 9010, and modified fluorocarbons.

Non-limiting examples of surface modifiers for use in the present invention include slip and gloss additives, a number of which are available from Byk-Chemie, Germany.

Non-limiting examples of thermoplastic resins for use in the present invention include reactive and non-reactive thermoplastic resins such as, e.g., polyphenylsulfones, polysulfones, polyethersulfones, polyvinylidene fluoride, polyetherimides, polyphthalimides, polybenzimidazoles, acrylics, phenoxy resins, and polyurethanes.

Non-limiting examples of mold release agents for use in the present invention include waxes such as, e.g., carnauba wax.

The mixture of aromatic polycyanate compounds of the present invention is useful, inter alia, as thermosettable comonomers for the production of printed circuit boards and materials for integrated circuit packaging (such as IC substrates). The mixture is especially useful for formulating matrix resins for high speed printed circuit boards, integrated circuit packaging, and underfill adhesives. As a mixture of comonomers, it may also be used to adjust the amount of hydrocarbon in a thermoset matrix.

EXAMPLE 1

A. Synthesis and Characterization of a Mixture of Polyphenolic Compounds Based on Cyclohexane Dicarboxaldehyde and Phenol Phenol (598 g, 6.36 moles) and cyclohexane dicarboxaldehyde (74.2 g, 0.53 moles, mixture of 1,3- and 1,4-isomers; ratio of phenolic groups to aldehyde groups=6:1, equivalent ratio of phenol to cyclohexane dicarboxaldehyde=3:1) were added together in a 1-L 5-neck reactor. The mixture was heated to 50° C. with 500 rpm mechanical stirrer agitation. At 50° C. and atmospheric pressure, p-toluenesulfonic acid (PTSA) (1.3959 g total, 0.207% by weight) was added in six portions over 30 minutes. The temperature increased a few degrees with each PTSA addition. After the 6th PTSA addition, the temperature controller was set to 70° C. and vacuum was applied to the reactor. In order to avoid the reactor content flooding the rectifier, the reactor pressure was gradually decreased to remove water from the reaction solution. When the reflux had stopped, the reactor was vented and water (48 g) was added.

Water (79 g) and NaHCO$_3$ (0.6212 g) were added to neutralize the PTSA. When the reaction contents had cooled to room temperature, the entire contents were transferred to a 2-L separatory funnel. Methyl ethyl ketone (MEK) was added, and the contents were washed several times with water to remove PTSA-salt. The solvents and excess phenol were removed using a rotary evaporator, and the hot novolac was poured onto aluminum foil. The reaction of phenol with cyclohexane dicarboxaldehyde produced as the predominant product a tetraphenol possessing the following idealized structure (tetraphenol of dimethylcyclohexane):

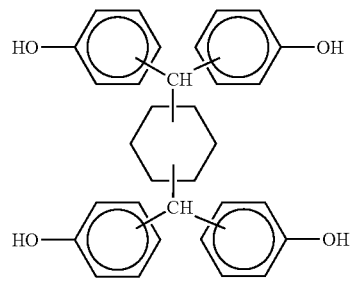

Ultraviolet spectrophotometric analysis provided a hydroxyl equivalent weight (HEW) of 118.64. High pressure liquid chromatographic (HPLC) analysis was adjusted to resolve 24 (isomeric) components present in the product.

B. Synthesis of the Tetracyanate of Dimethylcyclohexane

A 250 milliliter, three neck, glass, round bottom reactor was charged with the tetraphenol of dimethylcyclohexane (23.73 grams, 0.20 hydroxyl equivalent) and acetone (250 milliliters, 10.5 milliliter per gram of bisphenol). The reactor was additionally equipped with a condenser (maintained at 0° C.), a thermometer, an overhead nitrogen inlet (1 LPM N$_2$ used), a Claisen adaptor with septum, and mechanical stirring (glass shaft with Teflon™ blade and variable speed motor). Stirring commenced to give a solution at 22° C. Cyanogen bromide (22.67 grams, 0.214 mole, 1.07:1 cyanogen bromide:hydroxyl equivalent ratio) was added to the solution and immediately dissolved therein. A dry ice-acetone bath for cooling was placed under the reactor, followed by cooling and equilibration of the stirred solution at –5° C. Triethylamine (20.64 grams, 0.204 mole, 1.02 triethylamine:hydroxyl equivalent ratio) was added through the septum using a syringe in aliquots that maintained the reaction temperature at –6° C. to –2° C. The total addition time for the triethylamine was 40 minutes. After addition of the first three aliquots of triethylamine, a white slurry of triethylamine hydrobromide formed. After 15 minutes of post-reaction at –5° C. to –3° C., HPLC analysis of a sample of the reaction product revealed the expected retention time shift indicating complete conversion. This analysis was able to resolve 11 (isomeric) components in the tetracyanate product. After a cumulative 45 minutes of post-reaction at –5° C. to –2° C., HPLC analysis of a sample of the reaction product revealed no change in the product distribution. At this time, the product slurry was added to a beaker of magnetically stirred deionized water (2.0 liters) and dichloromethane (250 milliliters) providing a biphasic solution. After 3 minutes of stirring, the mixture was added to a separatory funnel, allowed to settle, and then the dichloromethane layer recovered, with the aqueous layer discarded to waste. The dichloromethane solution was added back into the separatory funnel and extracted with fresh deionized water (250 milliliters) 3 additional times. The resultant slightly hazy dichloromethane solution was dried over granular anhydrous sodium sulfate (15 grams) to give a clear solution which was then passed through a bed of anhydrous sodium sulfate (60 grams) supported on a 150 milliliter, medium fritted glass funnel attached to a side arm vacuum flask. The clear filtrate was rotary evaporated using a maximum oil bath temperature of 50° C. until the vacuum was <3.5 mm Hg. Further drying was completed for 28 hours at 50° C. in the vacuum oven. A total of 27.33 grams (95.13% uncorrected, isolated yield) of light golden yellow colored solid product was recovered. HPLC analysis of a sample of the product was identical to that previously obtained at the completion of the reaction.

EXAMPLE 2

Synthesis of the Homopolytriazine of the Tetracyanate of Dimethylcyclohexane

Differential scanning calorimetry (DSC) analysis of portions (8.5 and 8.9 milligrams, respectively) of the tetracyanate of dimethylcyclohexane from Example 1B above were completed using a rate of heating of 7° C. per minute from 25° C. to 400° C. under a stream of nitrogen flowing at 35 cubic centimeters per minute. A minor, reproducible, single melt endotherm was detected with an average midpoint of 91.02° C. accompanied by an enthalpy of 1.766 joules per gram. A single exotherm attributed to cyclotrimerization was detected with an average 151.6° C. onset, a 262.8° C. midpoint, and a 346.4° C. end accompanied by an enthalpy of 314.6 joules per gram. A glass transition temperature was not discernible from a second scanning of the resultant homopolytriazine. The homopolytriazine recovered from the DSC analysis was a transparent, amber colored, fused, rigid solid.

Although the present invention has been described in considerable detail with regard to certain versions thereof, other versions are possible, and alterations, permutations, and equivalents of the version shown will become apparent to those skilled in the art upon a reading of the specification and study of the drawings. Also, the various features of the versions herein can be combined in various ways to provide additional versions of the present invention. Furthermore, certain terminology has been used for the purposes of descriptive clarity, and not to limit the present invention. Therefore, any appended claims should not be limited to the description of the preferred versions contained herein and should include all such alterations, permutations, and equivalents as fall within the true spirit and scope of the present invention.

Having now fully described this invention, it will be understood to those of ordinary skill in the art that the methods of the present invention can be carried out with a wide and equivalent range of conditions, formulations, and other parameters without departing from the scope of the invention or any embodiments thereof.

What is claimed is:

1. A process for preparing a mixture of polycyanate compounds, wherein the process comprises partially or completely converting phenolic hydroxy groups in a mixture of polyphenolic compounds, wherein the polyphenolic compounds are prepared by a process comprising condensing a dialdehyde of a cycloalkane having from about 5 to about 24 ring carbon atoms with a phenolic compound at a ratio of phenolic hydroxy groups to aldehyde groups which affords a mixture of polyphenolic compounds with a polydispersity of not higher than about 2 and having an average number of hydroxy groups per molecule of at least 6, into cyanate groups.

2. The process of claim 1, wherein the molar ratio of phenolic hydroxy groups to aldehyde groups is at least about 4.

3. The process of claim 1, wherein the cycloalkane has from 6 to about 19 ring carbon atoms.

4. The process of claim 1, wherein the cycloalkane has 6, 7, or 8 ring carbon atoms.

5. The process of claim 1, wherein the dialdehyde comprises a cyclohexane dialdehyde.

6. The process of claim 1, wherein the phenolic compound comprises phenol.

7. A mixture of polyphenolic compounds which is obtainable by the process of claim 1.

8. The mixture of claim 7, wherein the polydispersity of the mixture is not higher than about 1.5.

9. The process of claim 1, wherein the process comprises contacting the mixture of polyphenolic compounds with a cyanogen halide.

10. The process of claim 1, wherein substantially all of the phenolic hydroxy groups are converted into cyanate groups.

11. A mixture of polycyanate compounds which is obtainable by the process of claim 1.

12. A mixture which comprises (i) the mixture of polycyanate compounds of claim 11 and/or a prepolymerized form thereof and (ii) at least one compound and/or prepolymer thereof which is capable of reacting with (i).

13. The mixture of claim 12, wherein the at least one compound (ii) is selected from one or more of aromatic di- and polycyanates which are different from polycyanates present in (i), aromatic di- and polycyanamides, di- and polymaleimides, and di- and polyglycidyl ethers.

14. The mixture of claim 12, wherein the mixture further comprises one or more substances which are selected from polymerization catalysts, co-curing agents, flame retardants, synergists for flame retardants, solvents, fillers, glass fibers, adhesion promoters, wetting aids, dispersing aids, surface modifiers, thermoplastic polymers, and mold release agents.

15. The mixture of claim 12, wherein the mixture is partially or completely cured.

16. A mixture which comprises (i) the mixture of polycyanate compounds of claim 11 and/or a prepolymerized form thereof and (ii) one or more substances which are selected from polymerization catalysts, co-curing agents, flame retardants, synergists for flame retardants, solvents, fillers, glass fibers, adhesion promoters, wetting aids, dispersing aids, surface modifiers, thermoplastic polymers, and mold release agents.

17. The mixture of claim 16, wherein the mixture is partially or completely cured.

18. A product which comprises a cured mixture of claim 12.

19. The product of claim 18, wherein the product is at least one of an electrical laminate, an IC substrate, a casting, a coating, a die attach and mold compound formulation, a composite, and an adhesive.

20. A tetraphenolic compound of formula (I):

wherein:
p is 0 or an integer of from 1 to about 19;
each m independently is 0, 1, or 2;

the moieties R independently represent halogen, cyano, nitro, optionally substituted alkyl, optionally substituted cycloalkyl, optionally substituted alkoxy, optionally substituted alkenyl, optionally substituted alkenyloxy, optionally substituted aryl, optionally substituted aralkyl, optionally substituted aryloxy, and optionally substituted aralkyloxy; and the moieties Q independently represent —CN, alkyl, alkenyl, aryl, aralkyl, and acyl;

and any non-aromatic cyclic moieties comprised in the above formula (I) may optionally carry one or more substituents and/or may optionally comprise one or more double bonds.

21. The compound of claim 20, wherein the moieties Q are identical.

22. The compound of claim 20, wherein substantially all moieties Q represent —CN.

23. The compound of claim 20, wherein p has a value of from 1 to about 14.

24. The compound of claim 20, wherein p has a value of 1, 2, or 3.

25. The compound of claim 20, wherein p equals 1.

26. The compound of claim 20, wherein each m independently is 0 or 1.

27. The tetraphenolic compound of claim 20, wherein the compound is dimethylcyclohexane tetraphenol tetracyanate.

* * * * *